United States Patent
Monaghan (10) Patent No.: US 9,775,628 B2
(45) Date of Patent: Oct. 3, 2017

(54) BONE RASP APPARATUS AND METHOD (71) Applicant: Zimmer, Inc., Warsaw, IN (US)

(72) Inventor: Matthew E. Monaghan, Fort Wayne, IN (US)

(73) Assignee: Zimmer, Inc., Warsaw, IN (US)

( * ) Notice: Subject to any disclaimer, the term of this patent is extended or adjusted under 35 U.S.C. 154(b) by 571 days.

(21) Appl. No.: 14/104,249

(22) Filed: Dec. 12, 2013

(65) Prior Publication Data

US 2014/0171951 A1   Jun. 19, 2014

Related U.S. Application Data (60) Provisional application No. 61/738,001, filed on Dec. 17, 2012.

(51) Int. Cl.
*A61B 17/00* (2006.01)
*A61B 17/16* (2006.01)

(52) U.S. Cl.
CPC ...... *A61B 17/1659* (2013.01); *A61B 17/1668* (2013.01)

(58) Field of Classification Search
None
See application file for complete search history.

(56) References Cited

U.S. PATENT DOCUMENTS

| | | |
|---|---|---|
| 4,552,136 A | 11/1985 | Kenna |
| 4,587,964 A | 5/1986 | Walker et al. |
| 4,601,289 A | 7/1986 | Chiarizzio et al. |
| 5,041,118 A | 8/1991 | Wasilewski |
| 5,261,915 A | 11/1993 | Durlacher et al. |
| 5,441,501 A | 8/1995 | Kenyon |
| 5,665,091 A | 9/1997 | Noble et al. |
| 5,704,940 A | 1/1998 | Garosi |
| 5,766,261 A | 6/1998 | Neal et al. |
| 5,993,455 A | 11/1999 | Noble |
| 6,224,605 B1 | 5/2001 | Anderson et al. |
| 6,319,256 B1 | 11/2001 | Spotorno et al. |
| 7,494,510 B2 | 2/2009 | Zweymuller |
| 7,998,211 B2 * | 8/2011 | Baccelli ............... A61F 2/4425 623/17.15 |
| 2007/0233127 A1 | 10/2007 | Tuke |
| 2010/0023014 A1 | 1/2010 | Romagnoli |
| 2010/0262146 A1 | 10/2010 | Tulkis |
| 2011/0160733 A1 | 6/2011 | Wallstein et al. |
| 2012/0095560 A1 * | 4/2012 | Donner ............... A61F 2/30988 623/17.11 |

* cited by examiner

*Primary Examiner* — Sameh Boles (74) *Attorney, Agent, or Firm* — Schwegman Lundberg & Woessner, P.A.

(57) ABSTRACT

In some examples, an apparatus includes a working surface including at least one material removal member. The material removal member is configured to remove at least some of a first portion of a first material. A protrusion extends outwardly from the working surface. The protrusion extends beyond the at least one material removal member by a first distance. The protrusion is configured to inhibit the at least one material removal member from removing at least a second portion of the first material. The second portion has a thickness substantially equal to the first distance.

20 Claims, 6 Drawing Sheets

BONE RASP APPARATUS AND METHOD

CLAIM OF PRIORITY

This application claims the benefit of U.S. Provisional Patent Application Ser. No. 61/738,001, filed on Dec. 17, 2012, the benefit of priority of which is claimed hereby, and of which is incorporated by reference herein in its entirety.

BACKGROUND

The present patent application relates to joint arthroplasty, and, more particularly, to a bone rasp apparatus and method for use in joint arthroplasty.

Orthopedic procedures for the replacement of all, or a portion of, a patient's joint have been developed over the last thirty years. Currently, the procedures used to prepare the bone and seat the implants are generally referred to as open procedures. For some joint arthroplasty procedures, such as hip and knee arthroplasty procedures, the preparation of the bone includes forming a channel within the bone within which to seat a portion of the artificial joint implant. Such bones typically include a hardened outer layer of compact bone surrounding an inner layer of spongy bone and/or marrow. Typically, reamers and rasps have been used by surgeons to form and size the channel by removing marrow and spongy bone along a length of the bone sufficient to accept the portion of the implant. Surgeons must be mindful to not remove too much spongy bone, however, and form too large of a channel for the intended implant. Being overly aggressive in rasping the spongy bone, for instance, can result in the removal of the spongy bone all the way down to the compact bone, which, in turn, can result in an oversized channel.

OVERVIEW

This overview is intended to provide an overview of subject matter of the present patent application. It is not intended to provide an exclusive or exhaustive explanation of the invention. The detailed description is included to provide further information about the present patent application.

The present inventor has recognized, among other things, that the subject matter can be used to prepare a bone for an artificial joint to aid in proper fitting and proper attachment of a portion (for instance, a stem) of the artificial joint within a channel of the bone.

To better illustrate the apparatus and method disclosed herein, a non-limiting list of examples is provided here:

Example 1 can include subject matter that can include an apparatus comprising a working surface including at least one material removal member, the material removal member being configured to remove at least some of a first portion of a first material. A protrusion extends outwardly from the working surface, the protrusion extending beyond the at least one material removal member by a first distance. The protrusion is configured to inhibit the at least one material removal member from removing at least a second portion of the first material, the second portion having a thickness substantially equal to the first distance.

In Example 2, the subject matter of Example 1 can optionally be configured such that the protrusion is configured to move within or through the first material and abut a second material, the first and second materials including adjacent layers. The protrusion is configured to space the material removal member from the second material by the first distance to inhibit the at least one material removal member from removing at least a second portion of the first material.

In Example 3, the subject matter of any one or any combination of Examples 1-2 can optionally be configured such that the working surface includes a plurality of material removal members.

In Example 4, the subject matter of any one or any combination of Examples 1-3 can optionally be configured such that the at least one material removal member includes a tooth extending from the working surface.

In Example 5, the subject matter of any one or any combination of Examples 1-4 can optionally be configured such that the protrusion extends along a length of the working surface.

In Example 6, the subject matter of any one or any combination of Examples 1-5 can optionally be configured such that the working surface includes more than one face, the faces oriented differently from one another.

In Example 7, the subject matter of Example 6 can optionally be configured such that each face of the more than one face of the working surface includes at least one protrusion.

In Example 8, the subject matter of any one or any combination of Examples 1-7 can optionally be configured such that the working surface includes two or more protrusions extending outwardly from the working surface, the two or more protrusions being spaced from one another.

In Example 9, the subject matter of Example 8 can optionally be configured such that the working surface includes the at least one material removal members disposed between the two or more protrusions.

Example 10 can include, or can optionally be combined with any one of Examples 1-9 to include subject matter that can include a method of using a material removal apparatus. The method comprises placing the material removal apparatus in contact with a first bone material. The apparatus includes: a working surface including at least one material removal member; and a protrusion extending outwardly from the working surface, the protrusion extending beyond the at least one material removal member by a first distance. At least some of a first portion of the first bone material is removed with the at least one material removal member. The protrusion is configured to inhibit the at least one material removal member from removing at least a second portion of the first bone material, the second portion having a thickness substantially equal to the first distance.

In Example 11, the subject matter of Example 10 is optionally configured such that removing at least some of a first portion of the first bone material includes moving the at least one material removal member relative to the first bone material with the at least one material removal member in contact with the first bone material.

In Example 12, the subject matter of Example 11 can optionally be configured such that moving the at least one material removal member relative to the first bone material causes the at least one material removal member to detach at least some of the first bone material from a remainder of the first bone material.

In Example 13, the subject matter of any one or any combination of Examples 11-12 can optionally be configured such that moving the at least one material removal member includes moving a plurality of teeth relative to the first bone material to wear away at least some of the first bone material from a remainder of the first bone material.

In Example 14, the subject matter of any one or any combination of Examples 10-13 can optionally be configured such that placing the material removal apparatus in contact with the first bone material includes placing the material removal apparatus within a channel of a bone.

In Example 15, the subject matter of any one or any combination of Examples 10-14 can optionally be configured such that removing at least some of the first portion of the first bone material includes moving the protrusion within or through the first bone material to abut a second bone material, the first and second bone materials including adjacent layers. The protrusion is configured to space the at least one material removal member from the second bone material by the first distance to inhibit the at least one material removal member from removing at least the second portion of the first bone material.

Example 16 can include, or can optionally be combined with any one or any combination of Examples 1-15 to include subject matter that can include an apparatus comprising a working surface including a plurality of teeth, the teeth being configured to remove at least some of a first portion of a first bone material. A protrusion extends outwardly from the working surface, the protrusion extending beyond the teeth by a first distance. The protrusion is configured to inhibit the teeth from removing at least a second portion of the first bone material, the second portion having a thickness substantially equal to the first distance. The protrusion is configured to move within or through the first bone material and abut a second bone material, the first and second bone materials including adjacent layers. The protrusion is configured to space the teeth from the second material by the first distance to inhibit the teeth from removing at least a second portion of the first bone material.

In Example 17, the subject matter of Example 16 can optionally be configured such that the working surface includes more than one face, the faces oriented differently from one another.

In Example 18, the subject matter of Example 17 can optionally be configured such that each face of the more than one face of the working surface includes at least one protrusion.

In Example 19, the subject matter of any one or any combination of Examples 17-18 can optionally be configured such that each face of the working surface includes two or more protrusions extending outwardly from the face of the working surface, the two or more protrusions being spaced from one another.

In Example 20, the subject matter of any one or any combination of Examples 16-19 can optionally be configured such that the protrusion includes an elongate rib extending along a length of the working surface substantially parallel to a longitudinal axis of the apparatus.

In Example 21 the subject matter of any one or any combination of Examples 1-20 can optionally be configured such that all elements, operations, or other options recited are available to use or select from.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present patent application relates to apparatuses and methods for removing material from a surface. For instance, the apparatuses and methods of the present application are used, in some examples, to remove material from a bone. In further examples, the apparatuses and methods are used to remove spongy bone and/or marrow from within a bone, for instance, to prepare and size a channel within a bone for placement of a portion of an artificial joint within the bone. The apparatuses and methods, in some examples, are used in various arthroplasty procedures, including knee arthroplasty procedures and hip arthroplasty procedures.

Figure 10:
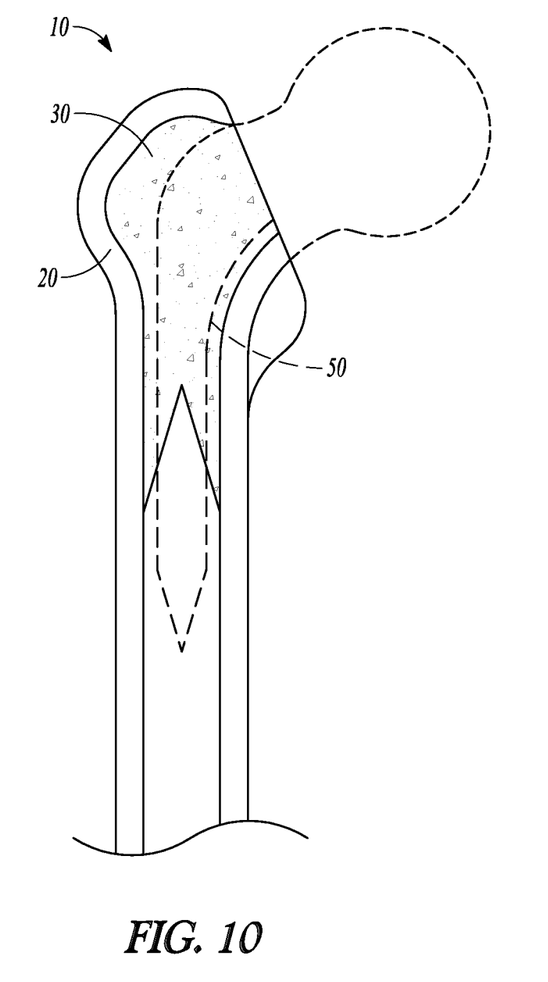
FIG. 10 is a cross-sectional view of a portion of a bone with which a bone rasp apparatus in accordance with at least one example of the invention can be used.

Referring to FIG. 10, during a typical arthroplasty procedure, a channel 50 is formed within a bone 10 to receive a portion of an artificial joint. Such bones 10 typically include a hardened outer layer 20 of compact bone surrounding an inner layer 30 of spongy bone and/or marrow. The channel 50 is typically formed by removing at least a portion of the inner layer 30 of spongy bone and/or marrow along a length of the bone 10 sufficient to accept the portion of the implant.

However, if too much of the spongy bone is removed, the resulting channel may be too large for the intended implant, which can lead to an ill-fitting implant. In some instances, the surgeon may opt to use a larger implant than intended to accommodate the larger channel. An ill-fitting or larger implant can result in the limb with the artificial joint being longer or shorter than intended, which can lead to various problems including symmetry problems with respect to the other limb. Also, it is generally considered to be beneficial to leave at least a portion of the spongy bone within the channel to provide a tighter fit between the bone and the implant and to promote ingrowth of the bone with respect to the implant and, in turn, better attachment of the implant within the bone. If the spongy bone is completely removed in one or more areas within the channel (i.e., down to the compact bone), poor attachment of the implant to the bone can result due to insufficient ingrowth of the bone with respect to the implant or due to play between the implant and the bone. Poor attachment of the implant can result in various issues, including movement or separation of the implant with respect to the bone or even failure of the implant.

To safeguard against at least the above-described problems, the present inventor has developed the apparatuses and methods described herein to inhibit surgeons from removing too much of the spongy bone from within a bone being prepared to receive an artificial joint.

Referring to FIGS. 1-6, in some examples, an apparatus 100 is configured for use in removing a material from a surface. In further examples, the apparatus 100 includes a bone rasp 100 configured to remove a bone material from a bone. Although the present description primarily refers to example bone rasps, it should be understood that the description herein can relate to rasps and material removers configured to remove materials other than bone, such as other body materials or tissues or materials outside the body such as foam, wood, or the like.

In some examples, the bone rasp 100 includes a shape configured to fit within a channel within a bone. For instance, the bone rasp 100 can include a distal end 100A having a relatively narrow profile. In further examples, the profile of the bone rasp 100 widens as from the distal end 100A to a proximal end 100B. In some examples, the shape of the bone rasp 100 is similar to a shape of a portion of an implant that is to be placed within the bone. For instance, the shape of the bone rasp 100 can be similar to the shape of a stem of a hip implant. Such a shape allows a surgeon to remove material, as described in more detail herein, from within the bone to create a similarly-shaped channel for accommodating the shape of the portion of the implant (for instance, the stem of the hip implant).

In some examples, the bone rasp 100 includes one or more attachment features for connecting the bone rasp 100 to a handle to allow gripping and manipulating of the bone rasp 100 by the surgeon. In some examples, the bone rasp 100 includes a first handle attachment feature 102 and a second handle attachment feature 104. The first and second handle attachment features 102, 104, in some examples, are configured to correspond to mating features of the handle to allow removable attachment of the handle with the bone rasp 100.

In the example shown in FIGS. 1-6, the first and second attachment features 102, 104 coordinate to securely attach the handle with the bone rasp 100 and inhibit rotation of the bone rasp 100 with respect to the handle. For instance, the first attachment feature 102 can include a shaft portion configured to couple to and in line with a shaft of the handle. In some examples, the first attachment feature 102 includes a notch 102A to accommodate a latch or other engagement feature of the handle to allow for releasable engagement of the handle with respect to the bone rasp 100. The second attachment feature 104 can be configured to inhibit rotation of the handle with respect to the bone rasp 100. In some examples, the second attachment feature 104 includes an opening 104A configured to accept a complementary protrusion of the handle. With the bearing of the protrusion of the handle within the opening 104A of the bone rasp 100, rotation of the handle with respect to the bone rasp 100 can be inhibited. It is noted that attachment of the handle and the bone rasp 100 can be accomplished in different ways in other examples, for instance, to accommodate differently configured handles and that the description of the first and second attachment features 102, 104 is merely exemplary. For instance, the present description contemplates bone rasps including differently shaped or configured attachment features, more or fewer than two attachment features, or an integrally attached handle.

In some examples, the bone rasp 100 includes at least one working surface 110 configured to remove material. The working surface 110 of the bone rasp 100, in some examples, can include an abrasive surface, which, when moved with respect to the material to be removed, functions to removed at least some of the material. In some examples, the working surface 110 includes at least one material removal member 120 (see FIGS. 7 and 8), the material removal member 120 being configured to remove at least some of a first portion of a first material. In some examples, the first material to be removed includes the inner layer 30 of spongy bone and marrow (FIG. 10). In some examples, the working surface 110 and the at least one material removal member 120 function to scrape, cut, or otherwise remove the inner layer 30 of spongy bone and marrow with back-and-forth movement of the bone rasp 100 within the channel 50. The material removal member 120, in some examples, includes a height A, as measured from a base of the material removal member 120 to an outward-most extending portion of the material removal member 120. In some examples, the working surface 110 includes a plurality of material removal members 120. The material removal members 120 can be disposed along the entire working surface 110, a portion of the working surface 110, or at two or more portions of the working surface 110.

Figure 1:
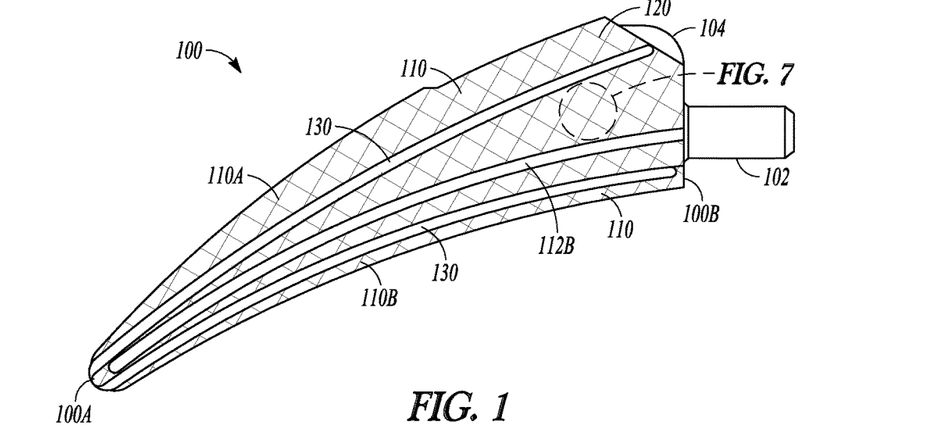
FIG. 1 is a side perspective view of a bone rasp apparatus in accordance with at least one example of the invention.
Figure 2:
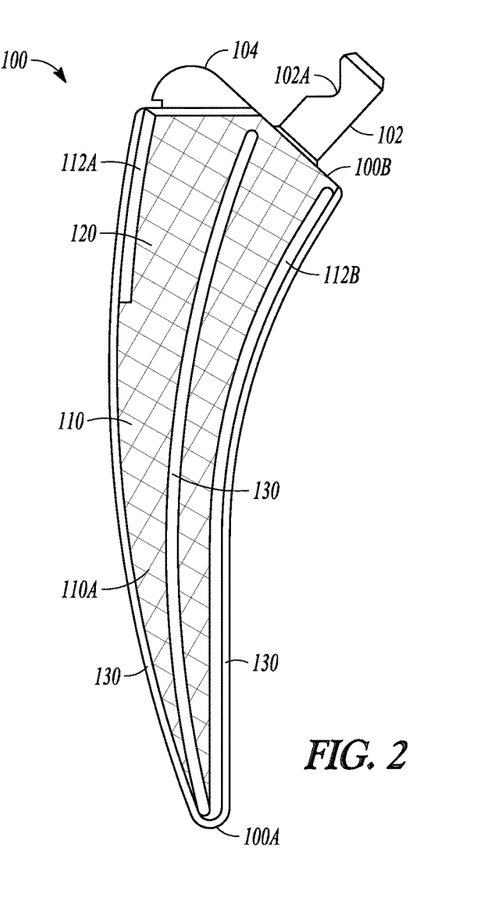
FIG. 2 is a side view of a bone rasp apparatus in accordance with at least one example of the invention.
Figure 3:
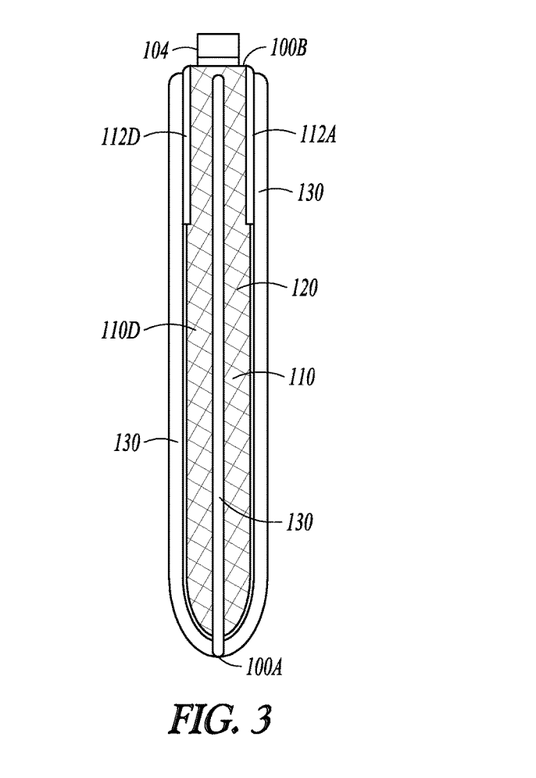
FIG. 3 is a front view of a bone rasp apparatus in accordance with at least one example of the invention.
Figure 4:
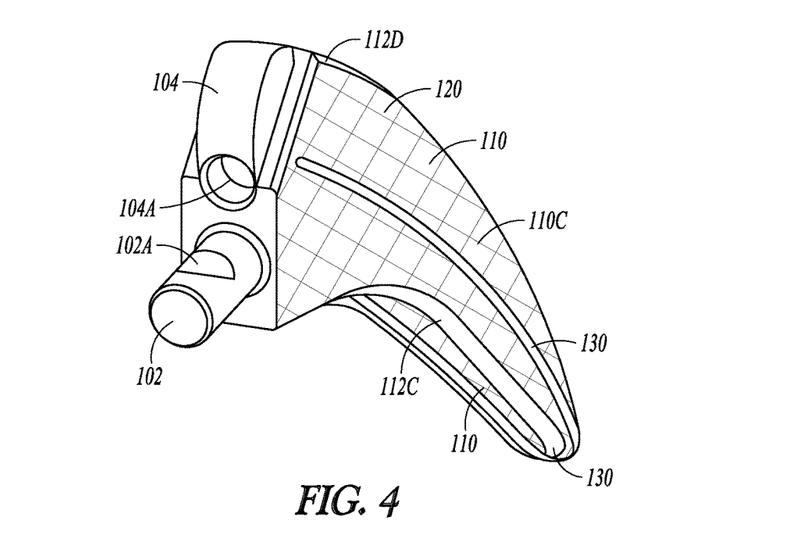
FIG. 4 is a top perspective view of a bone rasp apparatus in accordance with at least one example of the invention.
Figure 5:
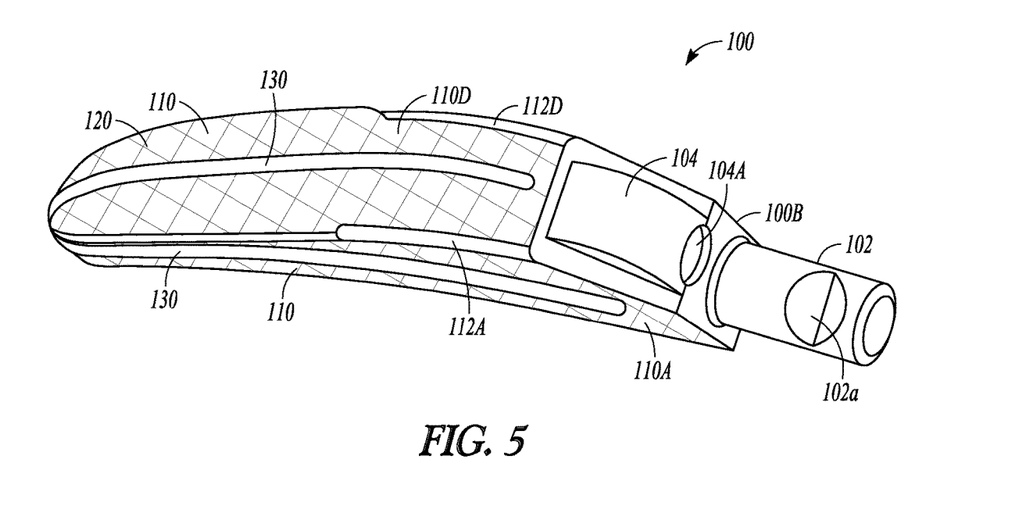
FIG. 5 is a front perspective view of a bone rasp apparatus in accordance with at least one example of the invention.
Figure 6:
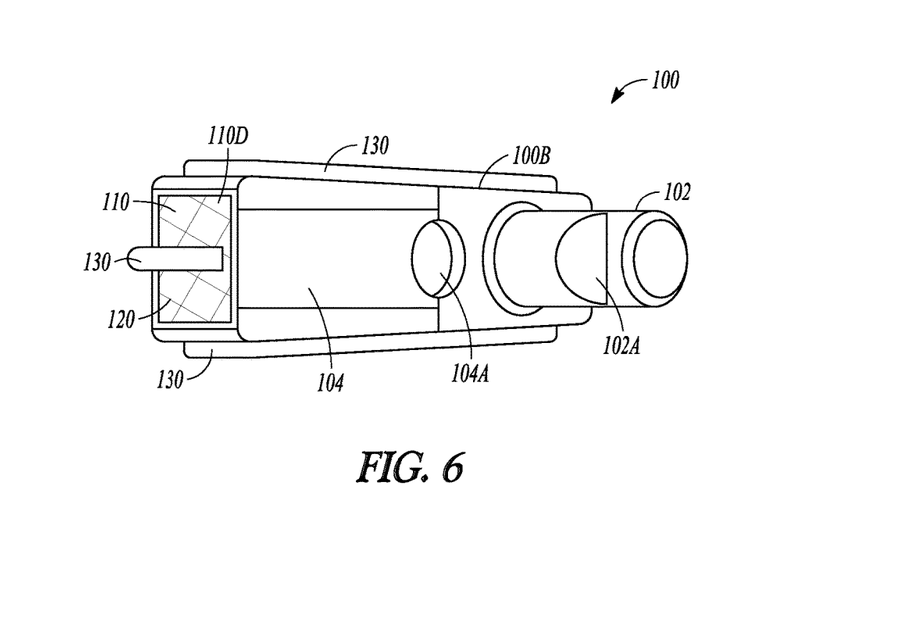
FIG. 6 is a top view of a bone rasp apparatus in accordance with at least one example of the invention.
Figure 7:
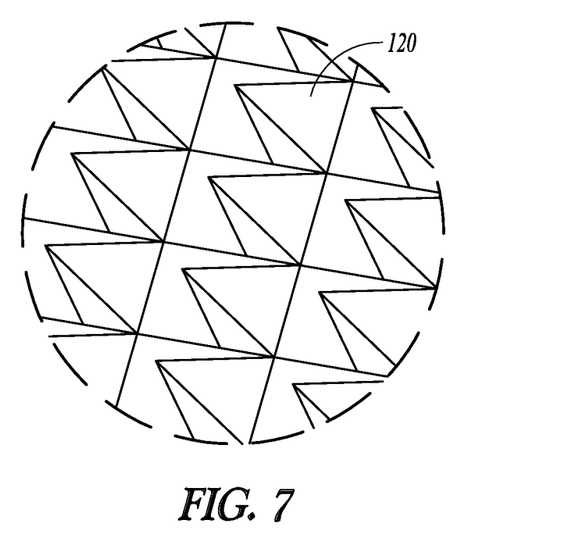
FIG. 7 is a close-up view of example teeth of the bone rasp apparatus of FIG. 1.

The one or more material removal members 120 can include various configurations. In some examples, the at least one material removal member 120 includes a tooth 120 extending from the working surface 110. Referring to FIG. 7, the tooth 120 can include a sharpened member extending from the working surface 110. In some examples, the one or more teeth 120 include a substantially triangular or pyramidal shape, such that at least a corner of the tooth 120 extends from the working surface 110 and is sufficiently sharp to be capable of cutting, scraping away, or otherwise removing a particular material from a surface. In some examples, the one or more teeth 120 are oriented on the working surface 110 such that the one or more teeth 120 are more effective in removing material with movement of the bone rasp 100 in one direction than in another, different direction. For instance, in an example, the one or more teeth 120 of the bone rasp 100 are oriented such that movement of the bone rasp 100 into the channel 50 allows removal of the material by the one or more teeth 120 but movement of the bone rasp 100 out of the channel 50 results in no (or at least lessened) removal of the material. In other examples, it is contemplated that the one or more teeth 120 are configured to remove material with movement of the bone rasp 100 in different directions within the channel 50 or other area from which material is to be removed. In some examples, the one or more teeth 120 are machined into the working surface 120. In other examples, the one or more teeth can be separately formed from the working surface and then inserted into or otherwise affixed to the working surface.

In some examples, the bone rasp 100 includes a protrusion 130 extending outwardly from the working surface 110. The protrusion 130 can include various configurations, such as an elongate rib, as is shown in FIGS. 1-6. In other examples, the protrusion can take other forms, as is described in more detail herein.

Figure 8:
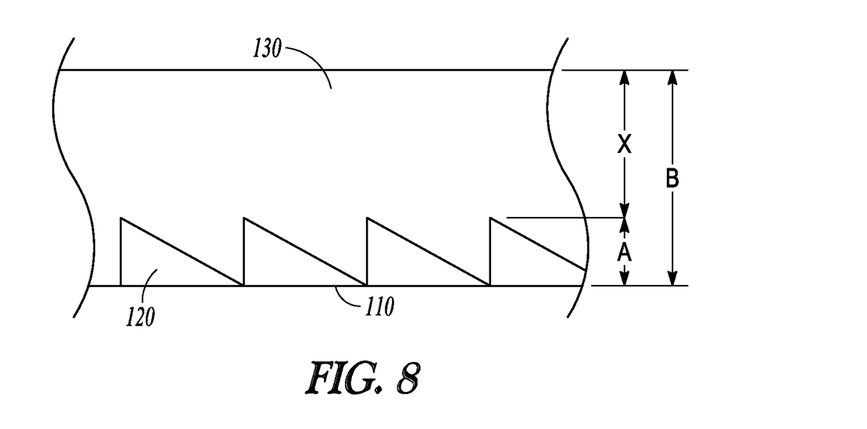
FIG. 8 is a simplified illustration of teeth and a spacing member of a bone rasp apparatus in accordance with at least one example of the invention.

In an example, the protrusion 130 includes a height B measured between an outermost edge of the protrusion 130 and the working surface 110 (FIG. 8). In some examples, the height B of the protrusion 130 is substantially similar along a length of the protrusion 130. In other examples, the height B of the protrusion 130 varies along the length of the protrusion 130. In some examples, the height B of the protrusion is greater than the height A of the at least one material removal member 120 at least at one location along the length of the protrusion 130. For instance, as shown in FIG. 8, the protrusion 130 extends beyond the at least one material removal member 120 by a first distance X. By extending beyond the at least one material removal member 120, the protrusion 130 is configured to inhibit the at least one material removal member 120 from removing at least a second portion of the first material, the second portion having a thickness substantially equal to the first distance X.

In some examples, the protrusion 130 extends along a length of the working surface 110. In further examples, the protrusion 130 extends along the entire length (or substantially the entire length) of the working surface 110. In other examples, the protrusion 130 extends along a portion of the length of the working surface 110. In some examples, the working surface can include two or more protrusions extending outwardly from the working surface, the two or more protrusions being spaced from one another. The protrusions can be separated from one another in at least one of a longitudinal direction of the bone rasp or a lateral direction of the bone rasp. In further examples, the working surface includes the at least one material removal members disposed between the two or more protrusions. In still further examples, the working surface includes a plurality of material removal members disposed between the two or more protrusions. In some examples, the protrusion 130 extends along the working surface 110 substantially parallel to a longitudinal axis of the bone rasp 100. In the example bone rasp 100 shown in FIGS. 1-6, the term "longitudinal axis" is used although the bone rasp 100 has a curvature to it. In this example, the longitudinal axis is used to mean a line running between the distal end 100A to the proximal end 100B of the bone rasp 100 and substantially conforming to the curvature of the bone rasp 100, the line being generally centrally disposed with respect to the bone rasp 100.

In some examples, the protrusion 130 is configured to move within or through the first material and abut a second material, the first and second materials including adjacent layers. For instance, with reference to FIG. 10, the protrusion 130 can be configured to move within or through the inner layer 30 of spongy bone and/or marrow but cannot penetrate the denser adjacent outer layer 20 of compact bone. Because the protrusion 130, in some examples, is unable or inhibited from penetrating the second material (for instance, the outer layer 20 of compact bone), the protrusion 130 acts as a spacer to inhibit the removal of a particular amount of the first material from within the channel 50. For instance, in some examples, the protrusion 130 is configured to space the material removal member 120 from the second material by the first distance X to inhibit the at least one material removal member 120 from removing at least a second portion of the first material.

That is, in some examples, the at least one material removal member 120 functions to remove the first portion of the first material, but, at the point where the protrusion 130 starts butting up against a second material (for instance, the hardened outer layer 20 of compact bone surrounding the inner layer 30 of spongy bone and/or marrow, as shown in FIG. 10) that the protrusion 130 is unable to pass through or within, the protrusion 130 acts as a bumper to inhibit the at least one material removal member 120 from further removing the first material, effectively leaving the second portion of the first material attached within the channel 50, which is substantially as thick as the first distance X. It is noted that the thickness of the second portion may vary slightly due to various factors including structure of the second material, direction of motion of the bone rasp 100 during removal of the first material, orientation of the bone rasp 100 during removal of the first material, effectiveness of the at least one material removal member 120 at removing the first material, or the like. Regardless of the potential of the slight variation in the thickness of the second portion of the first material, in some examples, the heights A, B of the at least one material removal member 120 and the protrusion 130, respectively, are such to maintain a sufficient thickness of the second portion for the given application. For instance, in the context of preparing a bone for insertion of a portion of a prosthetic joint implant, the heights A, B of the at least one material removal member 120 and the protrusion 130, respectively, of the bone rasp 100 are configured to allow an amount or thickness of the inner layer 30 of spongy bone and/or marrow to remain within the channel 50 in order to promote a proper fit of the portion of the implant within the channel 50 and ingrowth of bone with respect to the implant.

In some examples, the protrusion 130 is removable from the bone rasp 100. For instance, the protrusion 130 being removable allows for a surgeon or other user to remove the protrusion 130 and replace it with another, differently-sized protrusion for use with the bone rasp 100. The differently-sized protrusion can provide, for instance, a larger or smaller first distance X between the material removal member 120 and an edge of the protrusion to allow for more or less, respectively, material to be removed from within the channel 50 than the original protrusion 130 allowed. In another example, the removable protrusion 130 allows the surgeon or other user to remove the protrusion 130 and use the bone rasp 100 without a protrusion. Such removable protrusions, in some examples, are detachably retained within the bone rasp 100 using various engagement structures, such as, for instance, an interference fit between the protrusion and a channel within the bone rasp, a detent snap fit configuration, sliding engagement of the protrusion within a slot of the bone rasp, or other engagement configurations. In some examples, such removable or changeable protrusions allow for the surgeon or other user to change the extent to which the channel 50 is shaped, for instance, for the surgeon's or user's particular needs or the patient's particular needs, to better fit a desired gap or interference between the bone and the implant, to accommodate the surgeon's or other user's reaming/rasping technique, or to accommodate the patient's bone quality.

In some examples, the working surface 110 includes one or more faces disposed around the bone rasp 100. For instance, in some examples, the bone rasp 100 includes can include a substantially rectangular or square cross section at at least one or more points along a length of the bone rasp 100. In other examples, the bone rasp can include cross sections having different shapes, such as, but not limited to, triangular, hexagonal, octagonal, or other polygonal shapes; circular, elliptical, or other rounded shapes; or any other shape. At least one of the faces, in some examples, of the working surface 110 includes at least one protrusion 130. In some examples, each face of the more than one face of the working surface 110 includes at least one protrusion 130. In this way, the protrusions 130 can facilitate an amount or thickness of the inner layer 30 of spongy bone and/or marrow to remain within the channel 50 regardless of the orientation of the bone rasp 100 or the face of the bone rasp 100 used to remove material from within the channel 50.

In some examples, the faces of the working surface are oriented differently from one another. For instance, referring to FIGS. 1-6, the working surface 110 of the bone rasp 100 includes four faces 110A, 110B, 110C, 110D disposed around the bone rasp 100. Each of the faces 110A, 110B, 110C, 110D of the working surface 110 is disposed on a different side of the bone rasp 100. In some examples, one or more of the faces 110A, 110B, 110C, 110D of the working surface 110 include a curvature at least along a portion of the one or more faces 110A, 110B, 110C, 110D. Although the example bone rasp 100 shown in FIGS. 1-6 includes the working surface having four faces 110A, 110B, 110C, 110D, each disposed on a different side of the bone rasp 100, in other examples, the bone rasp can include a working surface having more or less than four faces or can include a side without a face of the working surface. That is, not all faces of a bone rasp are required to include one or more material removal members. For instance, the bone rasp 100 includes beveled corners 112A, 112B, 112C, 112D. The beveled corners 112A, 112B, 112C, 112D, in some examples, can include one or more material removal members, or, in other examples, the beveled corners 112A, 112B, 112C, 112D can include no material removal members, depending on various factors, including size of the area to be rasped, properties of the material to be rasped, and shape, size, and configuration of the bone rasp.

As shown in the example bone rasp 100 of FIGS. 1-6, the working surface 110 generally includes four faces 110A, 110B, 110C, 110D oriented around the bone rasp, with each of the faces 110A, 110B, 110C, 110D including a protrusion 130 extending from the respective face 110A, 110B, 110C, 110D. In some examples, each of the faces 110A, 110B, 110C, 110D includes a plurality of material removal members or teeth 120 configured to remove material, such as spongy bone and/or marrow, for instance, from a surface, such as, for instance, from within a bone. As described herein, the protrusions 130 of the example bone rasp 100 inhibit the material removal members 120 from removing an excess amount of material, for instance, by extending beyond the material removal members 120 and providing a space (the first distance X of FIG. 8) between the material removal members 120 and the top of the protrusion 130.

In some examples, more than one bone rasp 100 can be used to prepare a channel 50 within the bone 10. For instance, bone rasps 100 in sequential sizes can be used to allow the surgeon or other user to start with a relatively small bone rasp 100 to make an initial or small channel 50 and then increase the size of the channel 50 using one or more incrementally larger bone rasps 100. In some examples, the one or more protrusions 130 are located in different locations between the different bone rasps 100 so that the protrusions 130 of the different bone rasps 100 do not pass over the same portion of material between the different bone rasps 100 to inhibit remnant material within the channel 50. That is, if the protrusions 130 passed by the same area within the channel 50, material within the channel 50 corresponding to the position of the protrusions 130 would not be removed, which could lead to fit issues of the implant within the channel 50. By changing the placement of the protrusions 130 between different bone rasps 100, the bone rasps 100 allow for an amount of material, such as spongy bone and/or marrow, for instance, to remain within the channel 50 but inhibits one or more portions of the channel 50 from having little or no material removed.

Although shown with a single protrusion 130 running substantially down a middle of each of the faces 110A, 110B, 110C, 110D of the working surface 110 of the bone rasp 100, it is to be understood that such a configuration is merely exemplary and that further configurations of protrusions are contemplated. For instance, further examples of bone rasps 900A, 900B, 900C, 900D are shown in FIGS. 9A-9D. In these examples, several other examples of protrusions 930A, 930B, 930C, 930D are shown. Again, it is noted that these further examples are merely exemplary and are not meant to be limiting, as further examples of protrusions and bone rasps are contemplated herein.

Figure 9A:
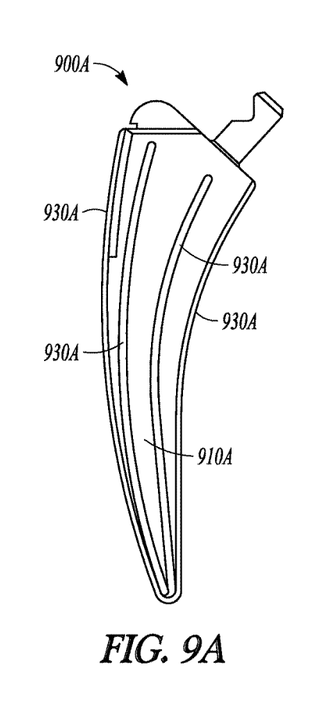
FIGS. 9A-9D are side views of a bone rasp apparatus in accordance with various embodiments of the invention.

Referring to FIG. 9A, the bone rasp 900A, in some examples, includes a working surface 910A of one or more faces. Although not described in detail, various examples of the bone rasp 900A, include one or more of the features of the examples of the bone rasps 100, 900B, 900C, 900D described herein. In some examples, the one or more faces of the working surface 910A include the protrusions 930A extending therefrom, for instance to inhibit material removal members (such as, for instance, teeth) from removing an excess amount of material. In some examples, at least one of the faces of the working surface 910A includes more than one protrusion 930A. In some examples, at least one face of the bone rasp 900A includes two elongate protrusions 930A that extend substantially along the length of the at least one face. In some examples, each of the protrusions 930A extends proximate an edge of the face. In this way, the protrusions 930A allow for spacing of the material removal members and inhibit excess removal of material, similar to that which is described herein with respect to the examples of the bone rasp 100, 900B, 900C, 900D. In some examples, the two protrusions 930A extending along the edges of the face provide for increased protection from removing an excessive amount of material from a single protrusion extending from the face in that the face of the bone rasp 900A, supported by the two protrusions 930A, is not as likely to tilt or teeter on the two protrusions 930A as it would be on a single protrusion. Tilting or teetering on a single protrusion could allow the material removal members (for instance, those material removal members spaced away from the protrusion) to be unhampered by the protrusion and remove more material than desired. As such, the material removal members of the face of the bone rasp 900A having two protrusions 930A extending from the face are less likely to remove an excessive amount of material because the protrusions 930A, acting in tandem, are not prone to tilting or teetering and, thereby, are not likely to allow the material removal members to come into contact with a hardened outer layer (for instance, of compact bone) and remove an excessive amount of material (for instance, spongy bone and/or marrow). In some examples, each face of the bone rasp 900A includes two protrusions 930A extending from the face. In some examples, at least one of the faces of the bone rasp 900A includes more than two protrusions 930A extending from the face.

Figure 9B:
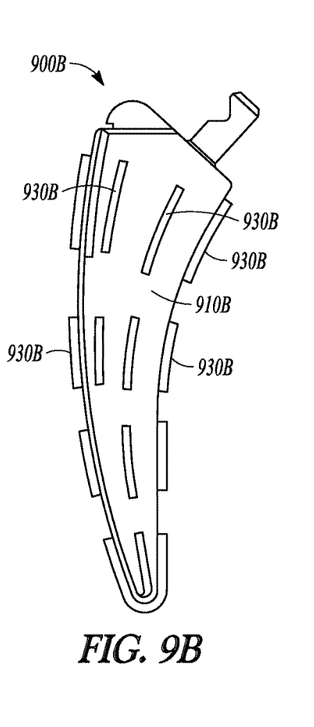

Referring now to FIG. 9B, the bone rasp 900B, in some examples, includes a working surface 910B of one or more faces. Although not described in detail, various examples of the bone rasp 900B, include one or more of the features of the examples of the bone rasps 100, 900A, 900C, 900D described herein. In some examples, the one or more faces of the working surface 910B include the protrusions 930B extending therefrom, for instance to inhibit material removal members (such as, for instance, teeth) from removing an excess amount of material. In some examples, at least one of the faces of the working surface 910B includes more than one protrusion 930B. In some examples, at least one face of the bone rasp 900B includes lines of segmented protrusions 930B that extend substantially along the length of the at least one face. In some examples, each of the lines of protrusions 930B extends proximate an edge of the face. In this way, the protrusions 930B allow for spacing of the material removal members and inhibit excess removal of material, similar to that which is described herein with respect to the examples of the bone rasp 100, 900A, 900C, 900D. In some examples, the lines of protrusions 930B extending along the edges of the face provide for increased protection from removing an excessive amount of material from a single protrusion extending from the face in a manner similar to that described with respect to the bone rasp 900A. In some examples, each face of the bone rasp 900B includes two lines of protrusions 930B extending from the face. In some examples, at least one of the faces of the bone rasp 900B includes more than two lines of protrusions 930B extending from the face.

Figure 9C:
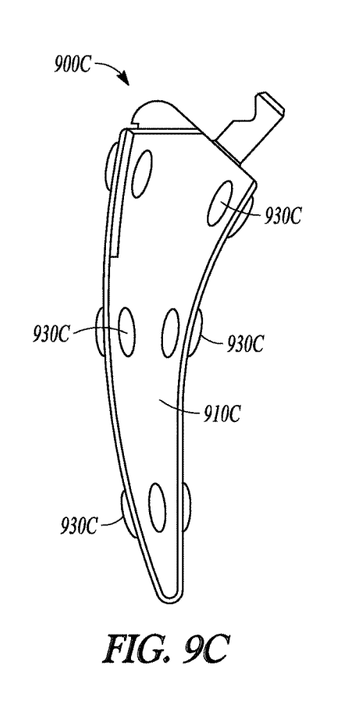

Referring now to FIG. 9C, the bone rasp 900C, in some examples, includes a working surface 910C of one or more faces. Although not described in detail, various examples of the bone rasp 900C, include one or more of the features of the examples of the bone rasps 100, 900A, 900B, 900D described herein. In some examples, the one or more faces of the working surface 910C include the protrusions 930C extending therefrom, for instance to inhibit material removal members (such as, for instance, teeth) from removing an excess amount of material. In some examples, at least one of the faces of the working surface 910C includes more than one protrusion 930C. In some examples, at least one face of the bone rasp 900C includes lines of elliptical curved protrusions 930C that extend substantially along the length of the at least one face. In some examples, each of the lines of protrusions 930C extends proximate an edge of the face. In this way, the protrusions 930C allow for spacing of the material removal members and inhibit excess removal of material, similar to that which is described herein with respect to the examples of the bone rasp 100, 900A, 900B, 900D. In some examples, the lines of protrusions 930C extending along the edges of the face provide for increased protection from removing an excessive amount of material from a single protrusion extending from the face in a manner similar to that described with respect to the bone rasp 900A. In some examples, each face of the bone rasp 900C includes two lines of protrusions 930C extending from the face. In some examples, at least one of the faces of the bone rasp 900C includes more than two lines of protrusions 930C extending from the face.

Figure 9D:
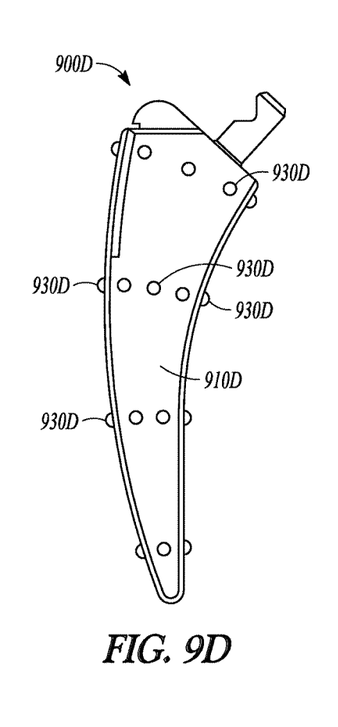

Referring now to FIG. 9D, the bone rasp 900D, in some examples, includes a working surface 910D of one or more faces. Although not described in detail, various examples of the bone rasp 900D, include one or more of the features of the examples of the bone rasps 100, 900A, 900B, 900C described herein. In some examples, the one or more faces of the working surface 910D include the protrusions 930D extending therefrom, for instance to inhibit material removal members (such as, for instance, teeth) from removing an excess amount of material. In some examples, at least one of the faces of the working surface 910D includes more than one protrusion 930D. In some examples, at least one face of the bone rasp 900D includes lines of semi-spherical or otherwise curved protrusions 930D that extend substantially along the length of the at least one face. In some examples, each of the lines of protrusions 930D extends proximate an edge of the face. In this way, the protrusions 930D allow for spacing of the material removal members and inhibit excess removal of material, similar to that which is described herein with respect to the examples of the bone rasp 100, 900A, 900B, 900C. In some examples, the lines of protrusions 930D extending along the edges of the face provide for increased protection from removing an excessive amount of material from a single protrusion extending from the face in a manner similar to that described with respect to the bone rasp 900A. In some examples, each face of the bone rasp 900D includes three lines of protrusions 930D extending from the face, with two lines of protrusions 930D proximate each of the sides of the face and one line of protrusions 930D in between the other two lines of protrusions 930D. In some examples, at least one of the faces of the bone rasp 900D includes more than three lines of protrusions 930D extending from the face.

Although various examples of bone rasps 100, 900A, 900B, 900C, 900D are described with various examples of protrusions 130, 930A, 930B, 930C, 930D, these examples are not intended to be limiting as other configurations of bone rasps and protrusions are contemplated herein, provided the protrusions are capable of inhibiting an excess amount of material (such as, for instance spongy bone or marrow) from being removed from a surface (for instance, an inner surface of a channel within a bone).

With reference to FIGS. 1-10 and continued reference to the description herein, in some examples, the present subject matter includes a method of using a material removal apparatus (such as, for instance, the bone rasp 100, 900A, 900B, 900C, 900D). In some examples, the method includes placing the bone rasp 100, 900A, 900B, 900C, 900D in contact with a first bone material (such as, for instance, the inner layer 30 of spongy bone or marrow). In some examples, the bone rasp 100, 900A, 900B, 900C, 900D includes a working surface 110, 910A, 910B, 910C, 910D including at least one material removal member 120. In some examples, the working surface 110, 910A, 910B, 910C, 910D includes a protrusion 130, 930A, 930B, 930C, 930D extending outwardly from the working surface 110, 910A, 910B, 910C, 910D. In some examples, the protrusion 130, 930A, 930B, 930C, 930D extends beyond the at least one material removal member by a first distance X, as described in more detail herein. In some examples, the method includes removing at least some of a first portion of the first bone material with the at least one material removal member 120. In some examples, the protrusion 130, 930A, 930B, 930C, 930D is configured to inhibit the at least one material removal member 120 from removing at least a second portion of the first bone material, the second portion having a thickness substantially equal to the first distance X.

In some examples, removing at least some of a first portion of the first bone material includes moving the at least one material removal member 120 relative to the first bone material with the at least one material removal member 120 in contact with the first bone material. For instance, the at least one material removal member 120 can be moved relative to the first bone material by moving the bone rasp 100, 900A, 900B, 900C, 900D back and forth within the channel 50. In other examples, the at least one material removal member 120 can be moved relative to the first bone material by moving the bone rasp 100, 900A, 900B, 900C, 900D side to side within the channel 50. In some examples, moving the at least one material removal member 120 relative to the first bone material causes the at least one material removal member 120 to detach at least some of the first bone material from a remainder of the first bone material. In some examples, the at least one material removal member 120 includes a plurality of teeth 120, wherein moving the plurality of teeth 120 relative to the first bone material wears away at least some of the first bone material from a remainder of the first bone material. In some examples, removing at least some of the first portion of the first bone material includes moving the protrusion 130, 930A, 930B, 930C, 930D within or through the first bone material to abut a second bone material (for instance, the outer layer 20 of compact bone), the first and second bone materials including adjacent layers, wherein the protrusion 130, 930A, 930B, 930C, 930D is configured to space the at least one material removal member 120 from the second bone material by the first distance X to inhibit the at least one material removal member 120 from removing at least the second portion of the first bone material.

The present inventor has recognized various advantages of the subject matter described herein. For instance, the example bone rasps 100, 900A, 900B, 900C, 900D described herein can be used, as described herein, to inhibit a surgeon or other user from removing too much of the spongy bone from within a bone being prepared to receive an artificial joint. In this way, the example bone rasps 100, 900A, 900B, 900C, 900D can be used to prepare a bone for an artificial joint to aid in proper fitting and proper attachment of a portion (for instance, a stem) of the artificial joint within the channel of the bone. While various advantages of the example bone rasps 100, 900A, 900B, 900C, 900D are listed herein, this list is not considered to be complete, as further advantages may become apparent from the description and figures presented herein.

Although the subject matter of the present patent application has been described with reference to various embodiments, workers skilled in the art will recognize that changes can be made in form and detail without departing from the scope of the invention recited in the below claims.

The above Detailed Description includes references to the accompanying drawings, which form a part of the Detailed Description. The drawings show, by way of illustration, specific embodiments in which the present locator apparatus and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The claimed invention is:

1. An apparatus used to remove a first material comprising at least one of a spongy bone material and a bone marrow material from within a femur, in order to prepare and size a channel within the femur for placement of a stem portion of an artificial hip joint within the channel, wherein the femur comprises the first material and a second material comprising a hardened outer layer of compact bone, the apparatus comprising:

a femoral stem body having a distal most end and a proximal most end, wherein the femoral stem body gradually tapers from the proximal most end toward the distal most end and has a shape similar to the stem portion of the artificial hip joint for placement within the channel;

a working surface located on the femoral stem body including at least one material removal member, the material removal member being configured to remove at least some of a first portion of the first material; and a protrusion extending outwardly from the working surface, the protrusion extending beyond the at least one material removal member by a first distance, the protrusion configured to inhibit the at least one material removal member from removing at least a second portion of the first material, the second portion having a thickness substantially equal to the first distance.

2. The apparatus of claim 1, wherein the protrusion is configured to move within or through the first material and abut the second material, the first and second materials including adjacent layers, wherein the protrusion is configured to space the material removal member from the second material by the first distance to inhibit the at least one material removal member from removing the second portion of the first material.

3. The apparatus of claim 1, wherein the working surface includes a plurality of material removal members.

4. The apparatus of claim 1, wherein the at least one material removal member includes a tooth extending from the working surface.

5. The apparatus of claim 1, wherein the protrusion extends along a length of the working surface.

6. The apparatus of claim 1, wherein the working surface includes more than one face, the faces oriented differently from one another.

7. The apparatus of claim 6, wherein each face of the more than one face of the working surface includes at least one protrusion.

8. The apparatus of claim 1, wherein the working surface includes two or more protrusions extending outwardly from the working surface, the two or more protrusions being spaced from one another.

9. The apparatus of claim 8, wherein the working surface includes the at least one material removal member disposed between the two or more protrusions.

10. The apparatus of claim 1, wherein the at least one material removal member is configured such that movement of the apparatus into the femur allows removal of at least some of the first portion of the first material.

11. The apparatus of claim 10, wherein movement of the apparatus out of the femur does not result in removal of the first portion of the first bone material.

12. The apparatus of claim 1, wherein the protrusion is removable from the working surface on the femoral stem body and comprises one of a plurality of differently-sized interchangeable protrusions.

13. An apparatus used to remove a first bone material comprising at least one of a spongy bone material and a bone marrow material from within a femur, in order to prepare and size a channel within the femur for placement of a stem portion of an artificial hip joint within the channel, wherein the femur comprises the first bone material and a second bone material comprising a hardened outer layer of compact bone, the apparatus comprising:
- a femoral stem body having a distal most end and a proximal most end, wherein the femoral stem body gradually tapers from the proximal most end toward the distal most end and has a shape similar to the stem portion of the artificial hip joint for placement within the channel;
- a working surface located on the femoral stem body including a plurality of teeth, the teeth being configured to remove at least some of a first portion of the first bone material; and
- a protrusion extending outwardly from the working surface, the protrusion extending beyond the teeth by a first distance, the protrusion configured to inhibit the teeth from removing at least a second portion of the first bone material, the second portion having a thickness substantially equal to the first distance, wherein the protrusion is configured to move within or through the first bone material and abut the second bone material, the first and second bone materials including adjacent layers, wherein the protrusion is configured to space the teeth from the second bone material by the first distance to inhibit the teeth from removing the second portion of the first bone material.

14. The apparatus of claim 13, wherein the working surface includes more than one face, the faces oriented differently from one another.

15. The apparatus of claim 14, wherein each face of the more than one face of the working surface includes at least one protrusion.

16. The apparatus of claim 14, wherein each face of the working surface includes two or more protrusions extending outwardly from the face of the working surface, the two or more protrusions being spaced from one another.

17. The apparatus of claim 13, wherein the protrusion includes an elongate rib extending along a length of the working surface substantially parallel to a longitudinal axis of the apparatus.

18. The apparatus of claim 13, wherein the teeth are configured such that movement of the apparatus into the femur allows removal of at least some of the first portion of the first bone material.

19. The apparatus of claim 18, wherein movement of the apparatus out of the femur does not result in removal of the first portion of the first bone material.

20. The apparatus of claim 13, wherein the protrusion is removable from the working surface on the femoral stem body and comprises one of a plurality of differently-sized interchangeable protrusions.

* * * * *